United States Patent [19]
Frey et al.

[11] Patent Number: 5,705,712
[45] Date of Patent: Jan. 6, 1998

[54] INTEGRATED PROCESS FOR PRODUCING DIISOPROPYL ETHER, AN ISOPROPYL TERTIARY ALKYL ETHER AND ISOPROPYL ALCOHOL

[75] Inventors: Stanley J. Frey, Palatine; Robert J. Schmidt, Barrington; Terry L. Marker, Warrenville; Richard E. Marinangeli, Arlington Heights, all of Ill.

[73] Assignee: UOP, Des Plaines, Ill.

[21] Appl. No.: 539,394

[22] Filed: Oct. 5, 1995

[51] Int. Cl.$^6$ ............................................. C07C 41/00
[52] U.S. Cl. ........................... 568/697; 568/698; 568/699
[58] Field of Search ................................... 568/697, 698, 568/699

[56] References Cited

U.S. PATENT DOCUMENTS

| | | | |
|---|---|---|---|
| 4,393,250 | 7/1983 | Gottlieb et al. | 568/697 |
| 5,011,506 | 4/1991 | Harandi et al. | 44/447 |
| 5,324,866 | 6/1994 | Marker et al. | 568/697 |
| 5,371,301 | 12/1994 | Marker et al. | 568/694 |

FOREIGN PATENT DOCUMENTS

92/08683  5/1992  WIPO.

*Primary Examiner*—Marianne M. Cintins
*Assistant Examiner*—Dwayne C. Jones
*Attorney, Agent, or Firm*—Thomas K. McBride; Eugene I. Snyder; Maryann Maas

[57] ABSTRACT

A highly integrated process for concurrently producing diisopropyl ether and an isopropyl tertiary alkyl ether has been developed. Optionally, high purity isopropyl alcohol may also be collected as a product. In a first reactor, propylene and water are reacted to form isopropyl alcohol, a portion of which is further reacted to form diisopropyl ether. After removing unreacted propylene, the effluent of the first reactor is separated into an ether rich stream, a water rich stream and an alcohol rich stream. The alcohol rich stream is dried to provide dry isopropyl alcohol. A portion of the dry isopropyl alcohol may be removed and collected as a product. A portion of the dry isopropyl alcohol and isobutylene, isoamylene or a mixture thereof are reacted to form an isopropyl tertiary alkyl ether in a second reactor. Unreacted iso-olefins and inert compounds are then removed from the second reactor effluent. A mixture of the effluent from the second reactor and the ether rich and the water rich streams separated from the first reactor are water washed to produce a mixed ethers product stream and an aqueous isopropyl alcohol recycle stream. The isopropyl tertiary alkyl ether is collected along with the diisopropyl ether in the mixed ethers product stream from the water wash. A modified flowscheme of the process is also discussed.

14 Claims, 2 Drawing Sheets

1

INTEGRATED PROCESS FOR PRODUCING DIISOPROPYL ETHER, AN ISOPROPYL TERTIARY ALKYL ETHER AND ISOPROPYL ALCOHOL

BACKGROUND OF THE INVENTION

As tetraethyl lead is phased out, oxygenates have become more important in the petroleum refining industry as a source of gasoline octane boosters. The most common oxygenates for this purpose are the dialkyl ethers, especially those in the $C_5$ to $C_8$ range. One example of such a dialkyl ether is diisopropyl ether which is in the boiling range of gasoline and has a high blending octane number of 105 and a blending Reid vapor pressure of 5. Furthermore, one reactant generally used in the formation of diisopropyl ether is propylene which is a by-product commonly available in refineries. The preparation of diisopropyl ether from propylene proceeds by two sequential reactions: (1) where propylene is first hydrated to isopropyl alcohol followed by reaction of the alcohol with the olefin, or (2) by a single bimolecular dehydration reaction of the alcohol (Williamson synthesis). Two more examples of desirable dialkyl ethers are isopropyl tertiary butyl ether and isopropyl tertiary amyl ether. Isopropyl tertiary butyl ether has a blending octane number of 113 and a blending Reid vapor pressure of 2.5. Isopropyl tertiary amyl ether has a blending octane number of 110 and a blending Reid vapor pressure of 2. These ethers may be produced through olefin etherification by reacting isopropyl alcohol with isobutylene and isoamylene, respectively, or by reacting propylene with tertiary butyl alcohol or tertiary amyl alcohol, respectively.

The preparation of diisopropyl ether from propylene and water is well known and numerous processes exist in the art such as U.S. Pat. No. 5,324,866 and U.S. Pat. No. 5,371,301. The production of isopropyl tertiary butyl ether and isopropyl tertiary amyl ether from reacting isopropyl alcohol with butylene and amylene is also known as demonstrated in U.S. Pat. No. 5,011,506 and U.S. Pat. No. 4,393,250.

Furthermore, U.S. Pat. No. 5,011,506 and WO 92/08683 disclose a process where excess isopropyl alcohol formed in a diisopropyl ether production reactor is separated, dewatered, and routed to an isopropyl tertiary alkyl ether production reactor where the isopropyl alcohol is reacted with iso-olefins to produce the isopropyl tertiary alkyl ethers. The isopropyl alcohol is dewatered using the iso-olefins feedstream as an extractant. The integration of the diisopropyl ether production process and the isopropyl tertiary alkyl ether production process occurs entirely prior to the isopropyl tertiary alkyl ether production reactor; there is no further integration of the processes downstream.

Applicants, however, are the first to realize that 1) a greater degree of integration between a diisopropyl ether production process and an isopropyl tertiary alkyl ether production process is possible; 2) the purity of the mixed ether product increases when the isopropyl alcohol is fully dried before use as a reactant in an isopropyl tertiary alkyl ether production reactor; and 3) an optional high purity isopropyl alcohol product stream may be collected. The higher degree of integration allows for the advantage of a single product stream of mixed oxygenates that does not have one discrete boiling point which would affect the shape of a gasoline distillation curve.

SUMMARY OF THE INVENTION

The purpose of the invention is to provide a highly integrated process for concurrently producing diisopropyl ether, an isopropyl tertiary alkyl ether, and, optionally, high purity isopropyl alcohol. In a first reactor, propylene and water are reacted to form isopropyl alcohol, a portion of which is further reacted to form diisopropyl ether. After removing unreacted propylene, the effluent of the first reactor is separated into an ether rich stream, a water rich stream and an alcohol rich stream. The alcohol rich stream is dried to provide dry isopropyl alcohol. A portion of the dry isopropyl alcohol may be removed and collected as a product. A portion of the dry isopropyl alcohol and isobutylene, isoamylene or a mixture thereof are reacted to form an isopropyl tertiary alkyl ether in a second reactor. Unreacted iso-olefins and inert compounds are then removed from the second reactor effluent. A mixture of the effluent from the second reactor and the ether rich and the water rich streams separated from the first reactor are water washed to produce a mixed ethers product stream and an aqueous isopropyl alcohol recycle stream. The isopropyl tertiary alkyl ether is collected along with the diisopropyl ether in the mixed ethers product stream from the water wash.

Another embodiment of the invention is one where the effluent from the first reactor, after removal of unreacted propylene, is passed to a drier to produce a dry isopropyl alcohol stream and an aqueous diisopropyl ether stream. As with the previous embodiment, a portion of the dry isopropyl alcohol may be removed and collected as a product. A portion of the dry isopropyl alcohol and isobutylene, isoamylene or a mixture thereof are reacted in a second reactor to form an isopropyl tertiary alkyl ether. After removal of unreacted iso-olefins and inert compounds, the effluent from the second reactor is passed to a water wash unit. The aqueous diisopropyl ether stream from the drier is allowed to separate into a diisopropyl ether enriched stream and a water enriched stream. The diisopropyl ether enriched stream is passed to the water wash unit and the water enriched stream is passed to a water rerun tower. In the water wash unit, the ethers are separated and withdrawn as a product stream, and an aqueous isopropyl alcohol stream is withdrawn and directed to the water rerun tower. In the water rerun tower, an isopropyl alcohol and water stream is separated and recycled to the first reactor, and a water stream is separated and passed to the water wash unit.

A more specific embodiment of the invention is one where catalyst degradation products are removed from the first reactor effluent before further processing.

DETAILED DESCRIPTION OF THE INVENTION

Figure 1:
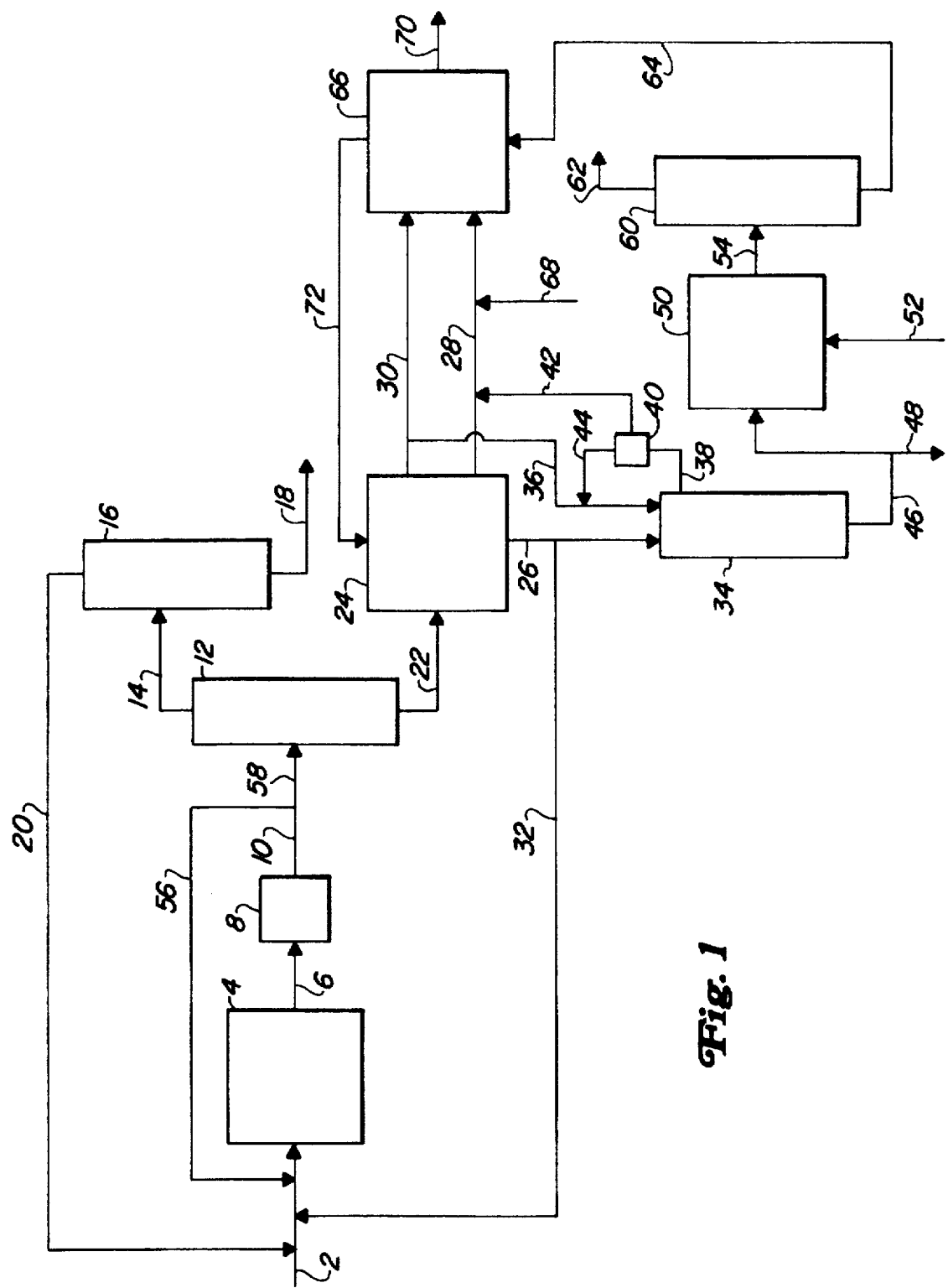
FIG. 1 is a schematic representation of the preferred embodiment of the invention.

The invention involves a highly integrated ether production process where at least diisopropyl ether and an isopropyl tertiary alkyl ether are concurrently produced. Optionally, high purity isopropyl alcohol may also be collected as a product. The integration of the processes involves introducing excess isopropyl alcohol from a diisopropyl ether reactor to an isopropyl tertiary alkyl ether reactor and concurrently water washing the effluents from both of the reactors to form a single mixed ethers product stream.

The process begins with water and a hydrocarbon feedstock containing propylene being introduced to a first reactor containing an acidic catalyst. The operating conditions of the first reactor include pressures of about 100 to about 1500 psig, preferably from about 700 to about 1000 psig, and temperatures of about 130° to about 180° C., preferably from about 135° to about 160° C. It is common to slowly increase the operating temperature as the catalyst ages. Suitable water to olefin mole ratios include from about 0.1:1 to about 0.8:1, preferably about 0.5:1. The propylene-containing hydrocarbon feedstock may be a refinery $C_3$ hydrocarbon stream and will most likely be a mixture of propylene and propane. The propylene-containing hydrocarbon feedstock should contain at least about 50 mass % propylene and preferably from about 70 to about 85 mass % propylene. Suitable sources for the propylene-containing hydrocarbon feedstock include, but are not limited to, gas plant off-gas containing propylene, naphtha cracker off-gas containing light olefins, propylene from a propane dehydrogenation process, and refinery fluidized catalytic cracked (FCC) propane/propylene streams.

The acidic catalyst contained in the first reactor may be any of those commonly used for a diisopropyl ether production process including acidic ion exchange resins, acidic zeolites, and supported heteropoly acids. The most preferred are the acidic ion exchange resins including sulfonated cation exchange resins such as sulfonated polystyrene resins and sulfonated styrene/divinylbenzene co-polymers. An example of a suitable sulfonated styrene/divinylbenzene co-polymer catalyst is Purolite CT-175 sold by Purolite; two more examples of preferred catalysts include Amberlyst® 36 and Amberlyst® 16. These sulfonated cation exchange resins are common in the art and do not require discussion here. For reference, see U.S. Pat. No. 5,371,301, G.B. 1,176,620, and U.S. Pat. No. 4,182,914. Halogenated strong acid ion exchange resins such as those described in U.S. Pat. No. 4,705,808, U.S. Pat. No. 4,269,943, and U.S. Pat. No. 3,256,250 may also be used. Suitable zeolitic catalysts are described in U.S. Pat. No. 5,011,506, and suitable supported heteropoly acids are described in U.S. Pat. No. 3,996,298 and U.S. Pat. No. 3,758,615.

As the propylene and water contact the catalyst, the hydration reaction takes place and isopropyl alcohol is formed. As isopropyl alcohol and propylene contact the catalyst, an etherification reaction takes place and diisopropyl ether is formed. Bimolecular dehydration of the isopropyl alcohol may also take place to form diisopropyl ether, but it is less preferred due to the increased consumption of isopropyl alcohol as compared to the etherification reaction. Therefore, the first reactor effluent is a mixture of water, propylene, isopropyl alcohol, and diisopropyl ether.

Catalyst degradation products may also be present in the first reactor effluent. An example of a particular acidic ion exchange resin catalyst degradation product is acid. Since catalyst deactivation may be accelerated by recycling a portion of the reactor effluent which contains catalyst degradation products to the reactor, the reactor effluent may be treated to remove the catalyst degradation products. For example, where the catalyst degradation product is acid, the effluent may be passed through an acid removal zone which contains solid particles capable of removing acid from the reactor effluent. Such solid particles include alkaline metal oxides, basic ion exchange resins, basic organically-bridged polysilsesquioxane particles, or any other strongly basic inorganic compounds with reasonable thermal stability, considering the reactor effluent will be at temperatures from about 130° C. to about 160° C. Activated carbon is also suitable. Other degradation products may be removed using similar commonly known means.

At least a portion of the first reactor effluent is recycled to the reactor to react the propylene and isopropyl alcohol to form diisopropyl ether and to control the temperature in the reactor. Suitable recycle ratios range from about 2:1 to about 15:1 and preferably about 5:1. The remainder of the first reactor effluent is first treated to remove light material and then separated into an ether enriched stream, an alcohol enriched stream, and a water enriched stream. The removal of light material is accomplished in a first light ends fractionation zone where compounds such as propylene and propane are removed. The first light ends fractionation zone may be operated at a temperature of about 80° C. and a pressure of about 235 psig. The separated light compounds such as propylene and propane may then be passed to a propylene/propane fractionation column where propane and propylene are separated into two streams. The propane enriched stream may be collected, and the propylene enriched stream may be recycled to the reactor. The recycled propylene enriched stream may contain as little as 50 mass % propylene, preferably from about 70 to about 85 mass % propylene, thereby eliminating the need for the expensive equipment required to obtain high purity propylene. The separated heavier compounds such as water, isopropyl alcohol, and diisopropyl ether are passed from the first light ends fractionation zone to a separator.

The separator is a fractionation column operating at from about 65° C. to about 125° C. and from about 25 to about 125 psig which separates the heavier compounds into a diisopropyl ether enriched stream, a water enriched stream, and an isopropyl alcohol enriched stream. Note that without further drying, the isopropyl alcohol enriched stream contains from about 5 to about 20 mass % water. A portion of the alcohol enriched stream is recycled to the first reactor to increase the conversion of isopropyl alcohol to diisopropyl ether and a portion of the isopropyl alcohol enriched stream is passed first to a drier and then to a second reactor to form isopropyl tertiary alkyl ether.

The isopropyl alcohol enriched stream is passed to a drier to remove water that is present in the stream. The drier is a fractionation column that may be operated at about 50° C. to about 150° C. and about 25 to about 125 psig. To aid in removing the water from the isopropyl alcohol, an entrainer may be added to the drier. The most preferred entrainer is diisopropyl ether which is also readily available from the first reaction zone. A portion of diisopropyl ether, or other suitable entrainer, is continuously recycled through the drier and removed in an aqueous stream. Upon removal, the diisopropyl ether and the water of the aqueous stream readily separate into two phases in a separator and the diisopropyl ether is recycled to the drier. The water is typically passed to a downstream water wash unit, but may be recycled to the first reaction zone instead. The drier may also be an adsorbent column containing solid particles capable of removing the water from the isopropyl alcohol. Suitable adsorbents include 3Å, 4Å, and 13X molecular sieves. The dry isopropyl alcohol stream exiting the drier should typically contain from about 100 to about 300 ppm water, or less, but should not contain more than about 1000 ppm water. If desired, a portion of the dry isopropyl alcohol stream exiting the drier may be removed and collected as a highly pure isopropyl alcohol product. The rest of the dry isopropyl alcohol may be passed to a second reactor to form isopropyl tertiary alkyl ether.

The operating conditions of the second reactor include pressures of about 100 to about 300 psig, preferably from about 100 to about 175 psig, and temperatures of about 30° C. to about 100° C., preferably from about 40° C. to about 80° C. It is common to slowly increase the operating temperature as the catalyst ages. A feed stream containing isobutylene, isoamylene, or a mixture thereof is also introduced to the second reactor. Suitable isopropyl alcohol to iso-olefin mole ratios include from about 3:1 to about 2.5:1. The iso-olefin-containing stream may be a refinery $C_4$ and/or $C_5$ hydrocarbon stream and will most likely be a mixture of isomeric $C_4$ and/or $C_5$ olefins and paraffins. Suitable sources for the iso-olefin-containing hydrocarbon feedstock include, but are not limited to, iso-olefins from a $C_4/C_5$ dehydrogenation process and refinery fluidized catalytic cracked $C_4/C_5$ streams. These streams typically also contain a significant amount of inert material.

The catalyst used in the second reactor may be any of those discussed above as suitable for use in the first reactor. The preferred catalyst is a macroporous acid form sulfonic ion exchange resin such as the sulfonated styrene-divinyl benzene resin described in U.S. Pat. No. 2,922,822. Other suitable resins include copolymers of sulfonyl fluorovinyl ether, fluorocarbons, and $SiO_2$-modified cation exchangers as described in U.S. Pat. No. 3,784,399, U.S. Pat. No. 3,849,243, and U.S. Pat. No. 4,751,343. Particularly suitable and preferred catalysts are sold under the designations Amberlyst® 35 and Amberlyst® 36 by Rohm and Haas. It is further contemplated that suitable catalysts include metal-containing resins which contain one or more metals from the sub-groups VI, VII or VIII of the Periodic Table such as chromium, tungsten, palladium, nickel, platinum, or iron as described in U.S. Pat. No. 4,330,679. Other catalysts include acidic shape-selective acidic zeolites or clays. Suitable zeolites may be of intermediate pore size such as ZSM-5 or of a large pore size such as zeolite-Y, zeolite beta, and ZSM-12. These zeolites and additional suitable zeolites are discussed in U.S. Pat. No. 5,011,506.

As the iso-olefin and isopropyl alcohol contact the catalyst in the second reactor, an etherification reaction takes place and isopropyl tertiary alkyl ether is formed. If the iso-olefin is isobutylene, then isopropyl tertiary butyl ether is formed, and if the iso-olefin is isoamylene, then isopropyl tertiary amyl ether is formed. If both isobutylene and isoamylene are present, both isopropyl tertiary butyl ether and isopropyl tertiary amyl ether are formed. For ease of understanding, the term "isopropyl tertiary alkyl ether" is used herein to refer to isopropyl tertiary butyl ether, isopropyl tertiary amyl ether, or the mixture thereof, whichever is present. Therefore, the second reactor effluent contains a mixture of iso-olefin, isopropyl alcohol and isopropyl tertiary alkyl ether.

The second reactor effluent is passed to a second light ends fractionation zone for removal of compounds such as iso-olefins and other inert hydrocarbons typically containing about 4 or 5 carbon atoms that are often present in the iso-olefin feed to the second reactor. The second light ends fractionation zone may be operated at a temperature of about 60° C. and a pressure of about 70 psig. The separated light compounds may be passed to other processes in a refinery and the remainder is passed to a water wash unit.

At least three streams are introduced to the water wash unit: 1) the separated heavier compounds such as isopropyl alcohol and isopropyl tertiary alkyl ether from the second light ends fractionation zone, 2) the diisopropyl ether rich stream from the separator, and 3) the water rich stream from the separator. Additional water may be added to the water wash unit as necessary, and the water that was removed in the isopropyl alcohol drier may be recycled to the water wash unit. The water wash unit is operated at a temperature of about 40° C. to about 80° C. and a pressure of about 150 to about 200 psig. Two streams are produced: an isopropyl alcohol and water stream and a mixed ethers stream containing diisopropyl ether and isopropyl tertiary alkyl ether. It is expected that the mixed ethers stream will contain greater than 96 mass % ethers. The isopropyl alcohol and water stream is recycled to the separator and the mixed ethers stream is collected.

The invention may also be practiced using a modified flowscheme. In the modified flowscheme, the stream containing water, isopropyl alcohol, and diisopropyl ether from the first light ends fractionation zone is passed directly to the isopropyl alcohol drier without first going to a separator. As in the above embodiment, the isopropyl alcohol drier is a fractionation column operated at about 50° C. to about 150° C. and about 25 to about 125 psig. The stream containing water, isopropyl alcohol, and diisopropyl ether is introduced to the drier and the diisopropyl ether acts as an entrainer, thereby producing an aqueous diisopropyl ether stream which may contain some isopropyl alcohol and a dry isopropyl alcohol stream. The dry isopropyl alcohol stream usually contains from about 100 to about 300 ppm water, or less, and is directed to the second reaction zone as described in the above embodiment. A portion of the dry isopropyl alcohol stream may be collected as a high purity isopropyl alcohol product.

The aqueous diisopropyl ether stream readily separates into two phases in a separator. The diisopropyl ether rich phase is directed to a water wash unit, while the water rich phase which may contain some isopropyl alcohol is directed to a water rerun tower. The water wash unit is operated at a temperature of about 40° C. to about 80° C. and a pressure of about 150 to about 200 psig. A water recycle stream from the water rerun tower is also introduced to the water wash unit to provide a water feed. The effluent from the second reaction zone, after having been passed through the second light ends fractionation zone, is also introduced to the water wash unit. In the water wash unit the ethers are separated from the water and isopropyl alcohol. A mixed ether product stream containing diisopropyl ether and isopropyl tertiary alkyl ether is withdrawn from the water wash unit and collected. A stream containing water and isopropyl alcohol is also withdrawn from the water wash unit and is passed to a water rerun tower which is operated at about 50° C. to about 100° C. and about 25 to about 125 psig. The water rich phase from the separator is also introduced to the water rerun tower. In the water rerun tower, a water stream is separated by fractionation from a water and isopropyl alcohol stream. The water stream is recycled to the water wash unit, and the water and isopropyl alcohol stream is recycled to the first reaction zone.

Without intending any limitation of the scope of the present invention and as merely illustrative, the invention is explained below in specific terms as applied to a specific embodiment of the invention which is based on a design for a commercial scale unit. Referring to FIG. 1, a 70 mass % propylene-30 mass % propane feed 2, a water, isopropyl alcohol, propylene, propane, and diisopropyl ether recycle 56, an isopropyl alcohol-water azeotrope stream 32, and a propylene-containing recycle 20 are combined and introduced to a first reaction zone 4 which contains Amberlyst® 36 catalyst. Reaction zone 4 is operated at 150° C. and 1000 psig. In reaction zone 4, the hydrolysis of propylene is catalyzed and isopropyl alcohol is formed. Some of the isopropyl alcohol is then catalytically reacted with propylene to form diisopropyl ether. Concurrently, the high temperature of the reaction zone and the presence of water cause $SO_3$ to split off acidic ion exchange resin catalyst. Due to the presence of water, the $SO_3$ forms $H_2SO_4$ which is carried into the reaction mixture. Other oxo acids of sulfur such as $HSO_3^-$ or $HSO_4^-$ may be formed, but for ease of understanding, only $H_2SO_4$ will be discussed.

Reaction zone effluent 6 contains propylene, propane, water, isopropyl alcohol, diisopropyl ether, and $H_2SO_4$, is cooled to 80° C. via heat exchangers (not shown) before being passed to acid removal unit 8 which contains Amberlite® IRA-68 basic ion exchange resin and is operated at 80° C. and 975 psig. As fluid reaction zone effluent 6 contacts the Amberlite® IRA-68 basic ion exchange resin, $SO_4^=$ or $HSO^-$ from the reaction zone effluent is exchanged for 2 $OH^-$ or $OH^-$ from the resin which neutralizes the $H^+$, thereby resulting in an $H_2SO_4$-depleted stream 10. $H_2SO_4$-depleted stream 10 is divided into two portions, one portion, stream 56, is recycled to reaction zone 4, and one portion, stream 58, is passed to a first light ends recovery unit 12. The recycle rate is about 5:1.

Fractionation in first light ends recovery unit 12 at 80° C. and 235 psig results in a propane and propylene stream 14 which is passed to a propylene/propane fractionation column 16, and a water, isopropyl alcohol, and diisopropyl ether stream 22 which is passed to a separator column 24. In propylene/propane fractionation column 16, propane and propylene stream 14 is separated into a propane enriched stream 18 which is collected, and a propylene enriched stream 20 which contains about 85 mass % propylene and is recycled to reaction zone 4. In separator column 24 the water, isopropyl alcohol, and diisopropyl ether stream 22 is fractionated at 125° C. and 125 psig to form a water enriched stream 28, an aqueous alcohol stream 26, and an ether enriched stream 30. Aqueous alcohol stream 26 contains about 15 mass % water and about 80 mass % alcohol. A portion of aqueous alcohol stream 26 is recycled to reaction zone 4 via line 32, and water enriched stream 28 and ether enriched stream 30 are passed to a water wash unit 66.

Aqueous alcohol stream 26 is passed to a drier 34 operated at 150° C. and 125 psig. A diisopropyl ether-containing stream 36 is also introduced into drier 34. The diisopropyl ether acts as an entrainer and draws water from the isopropyl alcohol into stream 38 so that stream 38 is a mixture of water and diisopropyl ether. Stream 38 enters a separator 40 where a diisopropyl ether enriched phase readily separates from a water enriched phase. The diisopropyl ether enriched phase is removed from the separator via line 44 and recycled to the drier. The water enriched phase is removed from the separator via line 42 and is combined with line 28. The dry isopropyl alcohol from drier 34 contains about 100 ppm water and is removed in line 46. A portion of the dry isopropyl alcohol stream 46 may be removed in line 48 and collected as high purity isopropyl alcohol product. The remainder of the dry isopropyl alcohol in line 46 and a 7.5 mass % isobutylene-12.5 mass % isoamylene feed 52 is passed to a second reaction zone 50. Second reaction zone 50 contains Amberlyst® 35 catalyst and is operated at 60° C. and 150 psig. In second reaction zone 50 the etherification of isobutylene and isoamylene with isopropyl alcohol is catalyzed and isopropyl tertiary butyl ether and isopropyl tertiary amyl ether are formed. Due to the lower operating temperature of second reaction zone 50, it is not expected that significant amounts of acid from the catalyst will enter the reaction mixture. Second reaction zone effluent 54 contains isobutylene, isoamylene, isopropyl alcohol, isopropyl tertiary butyl ether, and isopropyl tertiary amyl ether. Second reaction zone effluent 54 is directed to a second light ends fractionation zone 60 operating at 60° C. and 70 psig. Fractionation of second reaction zone effluent 54 in second light ends fractionation zone 60 results in an inert compounds, isobutylene, and isoamylene stream 62 and an isopropyl alcohol, isopropyl tertiary butyl ether, and isopropyl tertiary amyl ether stream 64.

Stream 64 and streams 28 and 30 discussed earlier are introduced to water wash unit 66. A water feed 68 may be combined with stream 28 when additional water is necessary for optimal performance of the water wash unit. A mixed ether product stream 70 containing at least 96 mass % mixed ethers, i.e., diisopropyl ether, isopropyl tertiary butyl ether, and isopropyl tertiary amyl ether, is withdrawn from water wash unit 66 and collected. An aqueous alcohol stream 72 containing water and isopropyl alcohol is withdrawn from water wash unit 66 and recycled to separator 24.

Figure 2:
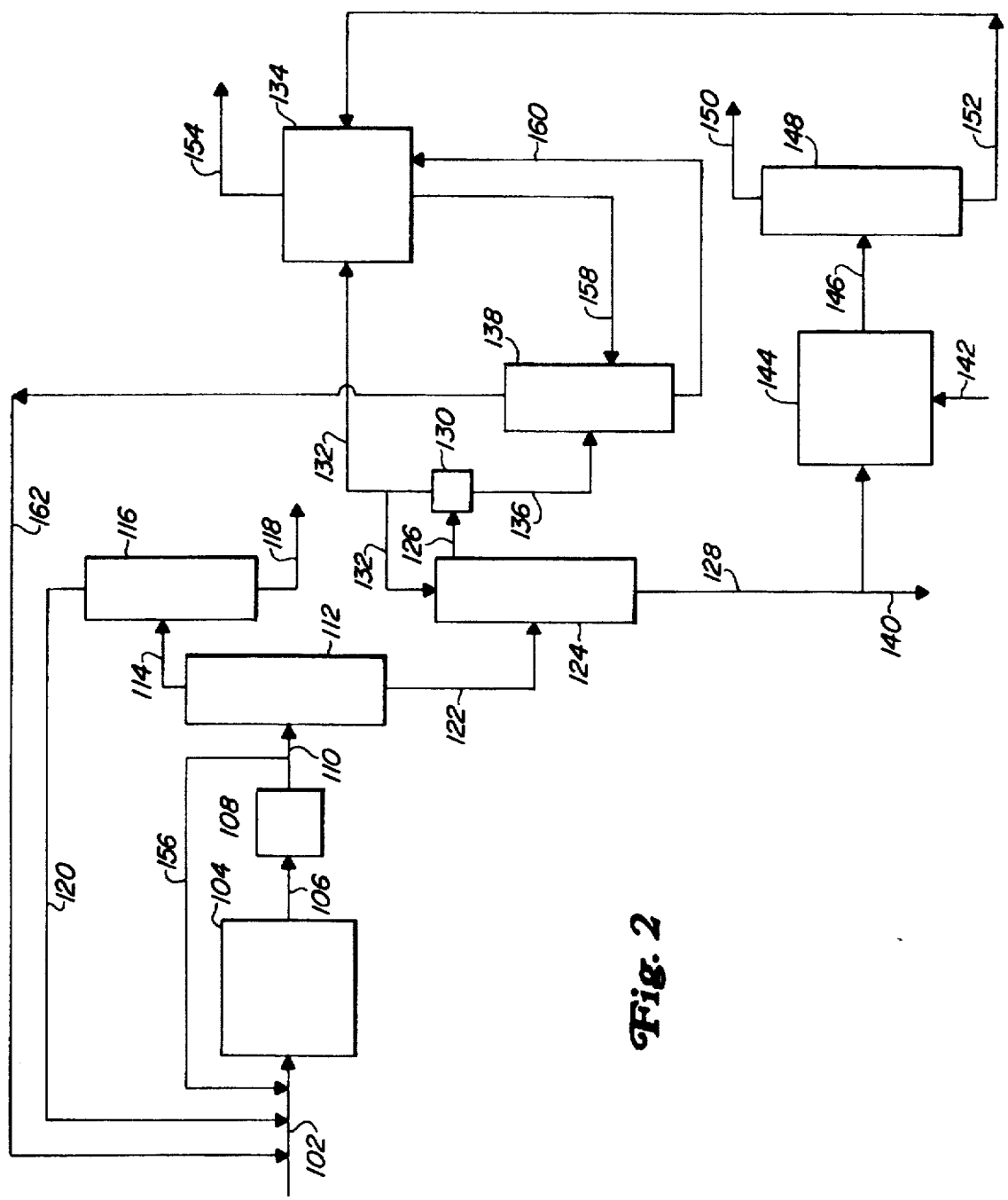
FIG. 2 is a schematic representation of another embodiment of the invention. The drawings have been simplified by the deletion of a large number of pieces of apparatus customarily employed in processes of this nature which are not specifically required to illustrate the performance of the subject invention.

Another specific embodiment of the invention is depicted in FIG. 2 where a 70 mass % propylene-30 mass % propane feed 102, a water, isopropyl alcohol, propylene, propane, and diisopropyl ether recycle 156, and a propylene recycle 120 are combined and introduced to a first reaction zone 104 which contains Amberlyst® 36 catalyst. Reaction zone 104 is operated at 150° C. and 1000 psig. In first reaction zone 104, the hydrolysis of propylene is catalyzed and isopropyl alcohol is formed. Some of the isopropyl alcohol is then catalytically reacted with propylene to form diisopropyl ether. Concurrently, the high temperature of the reaction zone and the presence of water cause $SO_3$ to split off from the acidic ion exchange resin catalyst. Due to the presence of water, the $SO_3$ forms $H_2SO_4$ which is carried into the reaction mixture. Other oxo acids of sulfur such as $HSO_3^-$ or $HSO_4^-$ may be formed, but for ease of understanding, only $H_2SO_4$ will be discussed.

Reaction zone effluent 106 contains propylene, propane, water, isopropyl alcohol, diisopropyl ether, and $H_2SO_4$, and is cooled to 80° C. via heat exchangers (not shown) before being passed to acid removal unit 108 which contains Amberlite® IRA-68 basic ion exchange resin and is operated at 80° C. and 975 psig. As fluid reaction zone effluent 106 contacts the Amberlite® IRA-68 basic ion exchange resin, $SO_4^=$ or $HSO_4^-$ from the reaction zone effluent is exchanged for $OH^-$ or 2 $OH^-$ from the resin which neutralizes the $H^+$, thereby resulting in an $H_2SO_4$-depleted stream 110. $H_2SO_4$-depleted stream 110 is divided into two portions: one portion, stream 156, is recycled to reaction zone 104, and the remainder is passed to a first light ends recovery unit 112. The recycle rate is about 5:1.

Fractionation in first light ends recovery unit 112 at 80° C. and 235 psig results in a propane and propylene stream 114, which is passed to a propylene-propane fractionation column 116, and a water, isopropyl alcohol, and diisopropyl ether stream 122, which is passed to a drier 124. In propylene-propane fractionation column 116, propane and propylene stream 114 is separated into a propane enriched stream 118, which is collected, and a propylene enriched stream 120, which contains about 85 mass % propylene and is recycled to reaction zone 104.

In drier 124, which is a fractionation column operated at 150° C. and 125 psig, water, isopropyl alcohol, and diisopropyl ether stream 122 is separated into two portions. The diisopropyl ether present in stream 122 acts as an entrainer and draws water from the isopropyl alcohol into a stream 126 so that stream 126 is a mixture of water and diisopropyl ether. Stream 126 enters a separator 130 where a diisopropyl ether enriched phase readily separates from a water enriched phase. The diisopropyl ether enriched phase is removed from the separator in line 132 and a portion is recycled to drier 124 with the remainder being passed to a water wash unit 134. The water enriched phase is removed from the separator in line 136 and is passed to a water rerun tower 138. The dry isopropyl alcohol from drier 124 contains about 100 ppm water and is removed in line 128. A portion of the dry isopropyl alcohol stream 128 may be removed in line 140 and collected as high purity isopropyl alcohol product. The remainder of the dry isopropyl alcohol in line 128 and a 7.5 mass % isobutylene-12.5 mass % isoamylene feed 142 is passed to a second reaction zone 144. Second reaction zone 144 contains Amberlyst® 35 catalyst and is operated at 60° C. and 150 psig. In second reaction zone 144 the etherification of isobutylene and isoamylene with isopropyl alcohol is catalyzed and isopropyl tertiary butyl ether and isopropyl tertiary amyl ether are formed. Due to the lower operating temperature of second reaction zone 144, it is not expected that significant amounts of acid from the catalyst will enter the reaction mixture. Second reaction zone effluent 146 contains isobutylene, isoamylene, isopropyl alcohol, isopropyl tertiary butyl ether, and isopropyl tertiary amyl ether.

Second reaction zone effluent 146 is directed to a second light ends fractionation zone 148 operating at 60° C. and 70 psig. Fractionation of second reaction zone effluent 146 in second light ends fractionation zone 148 results in an inert compounds, isobutylene, and isoamylene stream 150 and an isopropyl alcohol, isopropyl tertiary butyl ether, and isopropyl tertiary amyl ether stream 152. The inert compounds, isobutylene, and isoamylene stream 150 may be passed to other processes in a refinery. The isopropyl alcohol, isopropyl tertiary butyl ether, and isopropyl tertiary amyl ether stream 152 is passed to water wash unit 134. In water wash unit 134 an ether product stream 154 containing diisopropyl ether, isopropyl tertiary butyl ether, and isopropyl tertiary amyl ether is separated from an aqueous isopropyl alcohol stream 158. The ether product stream 152 is collected and the aqueous isopropyl alcohol stream 158 is passed to water rerun tower 138. In water rerun tower 138 a mainly isopropyl alcohol stream 162 is separated from a mainly water stream 160. The mainly isopropyl alcohol stream 162 is recycled to first reaction zone 104, and the mainly water steam 160 is passed to the water wash unit 134.

What is claimed is:

1. An integrated process for producing diisopropyl ether and an isopropyl tertiary alkyl ether comprising:
   a. reacting propylene, water, and isopropyl alcohol in the presence of a first acidic catalyst to afford a first reaction zone effluent;
   b. recycling a portion of the first reaction zone effluent to step (a) and removing propylene from the remainder to afford a propylene-depleted stream;
   c. separating the propylene-depleted stream into an ether enriched stream, an alcohol enriched stream, and a water enriched stream;
   d. drying the alcohol enriched stream to produce a dry alcohol stream;
   e. reacting the dry alcohol stream with isobutylene, isoamylene, or a mixture thereof present in a feed stream further containing inert compounds, in the presence of a second acidic catalyst to afford a second reaction zone effluent;
   f. removing the inert compounds, and isobutylene, isoamylene, or the mixture thereof from the second reaction zone effluent to afford an iso-olefin-depleted stream;
   g. water washing a mixture of the iso-olefin-depleted stream, the ether enriched stream, and the water enriched stream to afford an aqueous alcohol stream and an ether product stream;
   h. recycling the aqueous alcohol stream to step (c); and
   i. collecting the ether product stream.

2. The process of claim 1 where the dry alcohol stream contains less than about 1000 ppm water.

3. The process of claim 1 where the dry alcohol stream contains from about 100 to about 300 ppm water.

4. The process of claim 1 further comprising collecting a portion of the dry alcohol stream.

5. The process of claim 1 where the first acidic catalyst is selected from the group consisting of acidic ion exchange resins, acidic zeolites, and supported heteropoly acids.

6. The process of claim 1 where the second acidic catalyst is selected from the group consisting of acidic ion exchange resins, metal-containing resins, acidic zeolites, clays, copolymers of sulfonyl fluorovinyl ether, fluorocarbons and $SiO_2$-modified cation exchangers.

7. The process of claim 1 further comprising removing catalyst degradation products from the first reaction zone effluent prior to recycling.

8. The process of claim 1 further comprising removing acid from the first reaction zone effluent prior to recycling.

9. An integrated process for producing diisopropyl ether and an isopropyl tertiary alkyl ether comprising:
   a. reacting propylene, water, and isopropyl alcohol in the presence of a first acidic catalyst to afford a first reaction zone effluent;
   b. recycling a portion of the first reaction zone effluent to step (a) and removing propylene from the remainder to afford a propylene-depleted stream;
   c. drying the propylene-depleted stream to produce a dry alcohol stream and an aqueous ether stream;
   d. separating the aqueous ether stream into an ether enriched stream and a water enriched stream;
   e. separating the water enriched stream and an aqueous alcohol stream to produce an aqueous stream and a mainly alcohol stream;
   f. recycling the mainly alcohol stream to step (a);
   g. reacting the dry alcohol stream with isobutylene, isoamylene, or a mixture thereof present in a feed stream further containing inert compounds, in the presence of a second acidic catalyst to afford a second reaction zone effluent;
   h. removing the inert compounds, and isobutylene, isoamylene, or the mixture thereof from the second reaction zone effluent to afford an iso-olefin depleted stream;
   i. water washing a mixture of the iso-olefin depleted stream, the ether enriched stream, and the aqueous stream to afford the aqueous alcohol stream and an ether product stream;
   j. recycling the aqueous alcohol stream to step (e); and
   k. collecting the ether product stream.

10. The process of claim 9 where the dry alcohol stream contains less than about 1000 ppm water.

11. The process of claim 9 where the dry alcohol stream contains from about 100 to about 300 ppm water.

12. The process of claim 9 further comprising collecting a portion of the dry alcohol stream.

13. The process of claim 9 where the first acidic catalyst is selected from the group consisting of acidic ion exchange resins, acidic zeolites, and supported heteropoly acids.

14. The process of claim 9 where the second acidic catalyst is selected from the group consisting of acidic ion exchange resins, metal containing resins, acidic zeolites, clays, copolymers of sulfonyl fluorovinyl ether, fluorocarbons and $SiO_2$-modified cation exchangers.

* * * * *